US00PP08024P

United States Patent [19]

Suzuki

[11] Patent Number: Plant 8,024

[45] Date of Patent: Nov. 10, 1992

[54] ROSE PLANT— KEIZOUBO VARIETY

[75] Inventor: Seizo Suzuki, Chiba, Japan

[73] Assignee: The Conard-Pyle Company, West Grove, Pa.

[21] Appl. No.: 672,074

[22] Filed: Mar. 19, 1991

[51] Int. Cl.[5] ..... A01H 5/00

[52] U.S. Cl. ..... Plt./11

[58] Field of Search ..... Plt. 11, 15, 16, 17

[56] References Cited

U.S. PATENT DOCUMENTS

P.P. 4,868 7/1982 Meilland ..... Plt. 15

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which forms attractive double long lasting blossoms which are light tangerine orange on the upper side and Chinese yellow suffused with tangerine orange on the under side. The buds and blossoms are well shaped and are of a distinctive and very attractive configuration (as illustrated). Such coloration is relatively bright and is well maintained when the blossoms are cut and placed in a vase. The plant exhibits an upright growth habit, forms vigorous vegetation, and is well suited for cut flower production. Additionally, the plant is not particularly affected by cryptogamic diseases.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the pollination of the Elmera variety (non-patented in the United States) by the Meirilocra variety (U.S. Pat. Plant No. 4,868). The male parent (i.e., the pollen parent) was the Keivlanox variety (non-patented in the United States). The parentage of the new variety can be summarized as follows:

(Elmera × Meirilocra) × Keivlanox.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms attractive long lasting double blossoms which are light tangerine orange on the upper side and Chinese yellow suffused with tangerine orange on the under side,
(b) forms blossoms which well maintain their bright coloration when cut and placed in a vase,
(c) forms buds and blossoms which are of a particularly attractive configuration,
(d) exhibits vigorous vegetation,
(e) exhibits an upright growth habit,
(f) is particularly suited for cut flower production, and
(g) is not particularly affected by cryptogamic diseases.

The new variety well meets the needs of the horticultural industry and is particularly well suited for cut flower production.

The new variety has been found to undergo asexual propagation by a number of routes, including budding, grafting, cuttage, etc. A sexual propagation by the above mentioned methods as performed in France has shown that the characteristics of the new variety are strictly transmissible from one generation to another.

The new variety has been named the Keizoubo variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Cap d'Antibes, France.

DETAILED DESCRIPTION

Figures 1, 2, 3, 4, 5, 6, 7, 8, 9, 10, 11, 12, 13, 14, 15, 16:
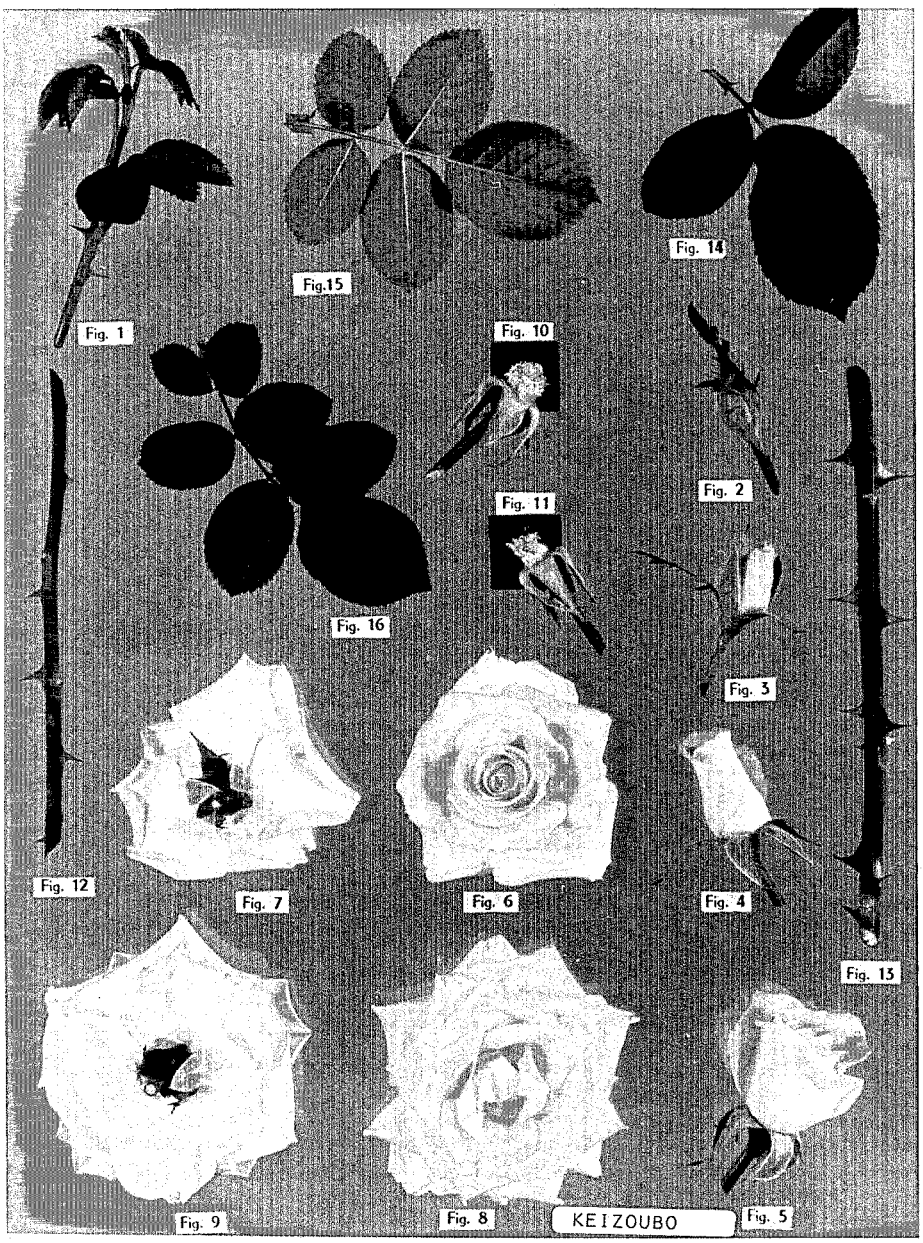
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of opening.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets—plan view—upper surface.
FIG. 15 illustrates a specimen of a leaf with five leaflets—plan view—under surface.
FIG. 16 illustrates a specimen of a leaf with seven leaflets—plan view—upper surface.

The chart used in the identification of the colors is that of The Royal Horticultural Society (R.H.S. Colour Chart). The description is based on the observation of two year old plants made during November while budded on *Rose indicia* understock and growing in outdoors at Cap d'Antibes, France. The coloration in common terms precedes reference to the chart.

Class: Hybrid Tea.

Plant:

*Height.*—Plants which were pruned to a height of 85 cm produce floral stems having a length of approximately 40 to 60 cm. When grown in a field at Wasco, Calif., one year old budded plants commonly assume a height of approximately 110 cm.

*Habit.*—Upright.

Branches:

*Color.*—Young stems: medium green, Yellow-Green Group 146B, more or less stained with reddish coloration. Adult wood: light green, Yellow-Green Group 146C.

*Thorns.*—Size: average. Quantity: low. Color: pinkish on young stems and greenish changing to tan on mature wood.

Leaves:

*Stipules.*—Adnate, pectinate, fairly wide and linear.

*Petioles.*—Upper surface: striped reddish brown on young foliage and medium green on adult foliage with glandular edges. Under surface: light green, and bear a few prickles.

*Leaflets.*—Number: 3 and 5 (most often), and 7. Shape: oval to elliptic. Serration: single and regular. Texture: consistent. General appearance: dense, semi-dull foliage. Color (young foliage): Upper surface: dark green, Yellow-Green Group 147A, stained with reddish coloration on edges. Under surface: medium geen, Yellow-Green Group 147B, shaded with reddish coloration. Color (adult foliage): Upper surface: dark green, Yellow-Green Group 147A. Under surface: medium green, Yellow-Green Group 147B.

Inflorescence:

*Number of flowers.*—Usually one single bloom per stem.

*Peduncle.*—Light Green and more or less stained with reddish coloration, bears small pediculate glands. The length is approximately 11 cm. on average.

*Sepals.*—Upper surface: tomentose, greenish in coloration. Under surface: medium green, and the outer sepals have appendiculate edges which sometimes end in a leaf-like appendix.

*Buds.*—Shape: conical. Length: approximately 4 cm. on average. Size: large. Color upon opening: Upper surface: tangerine orange, Orange Group 25 A. Under surface: Chinese Yellow, Yellow-Orange Group 16B, suffused on the edges with tangerine orange, Orange Group 25C.

*Flower.*—Shape: cup-like with substantially parallel sides, fully double. Diameter: approximately 10 cm. on average. Color (when opening begins): Upper surface: tangerine orange, Orange Group 25B. Under surface: Chinese yellow, Yellow-Orange Group 16B, lightly suffused on the edges with tangerine orange Orange Group 25C, and with lighter coloration on the outer petals. Color (when blooming): Upper surface: light tangerine orange, Orange Group 25C. Under surface: Chinese yellow, Yellow-Orange Group 16B, lightly suffused on the edges with tangerine orange Orange Group 25C, and with lighter coloration on the outer petals. Color (at end of opening): Upper surface: light tangerine orange, Orange Group 25C, and light orange, Orange Group 28D, on parts exposed to direct sunlight. Under surface: peach orange, Orange Group 29D, at the edges and light Chinese yellow, Yellow-Orange Group 16D toward the center of the petals. Fragrance: none. Lasting quality: long when cut and present in a vase. Petal number: approximately 30 to 38 on average. Petal shape: rounded. Texture: consistent. Petal drop: good. Stamen number: approximately 71 on average. Anthers: normal, bright yellow. Filaments: bright yellow, of irregular heights. Pistils: approximately 102 on average. Stigmas: normal, ochre in coloration. Styles: greenish in coloration with light fuschia tips, more or less twisted, of irregular heights. Receptacle: light green in coloration, in longitudinal section it is in the shape of a funnel.

Development:

*Vegetation.*—Very vigorous.

*Blooming.*—Average to good for a cut flower variety.

*Resistance to diseases.*—Good.

*Aptitude to be forced.*—Average.

I claim:

1. A new and distinct variety of Hybrid Tea rose plant characterized by the following combination of characteristics:

(a) forms attractive long lasting double blossoms which are light tangerine orange on the upper side and Chinese yellow suffused with tangerine orange on the under side, (b) forms blossoms which well maintain their bright coloration when cut and placed in a vase, (c) forms buds and blossoms which are of a particularly attractive configuration, (d) exhibits vigorous vegetation, (e) exhibits an upright growth habit, (f) is particularly suited for cut flower production, and (g) is not particularly affected by cryptogamic diseases;

substantially as herein shown and described.

* * * * *

KEIZOUBO